United States Patent [19]

Friddle

[11] Patent Number: 4,648,390
[45] Date of Patent: Mar. 10, 1987

[54] LOW PROFILE NECK RING ORTHOSIS

[76] Inventor: Frank E. Friddle, P.O. Box AR, Rte. 2, Honea Path, S.C. 29654

[21] Appl. No.: 735,376

[22] Filed: May 17, 1985

[51] Int. Cl.⁴ ............................ A61F 5/04; A61F 5/01
[52] U.S. Cl. .................................... 128/78; 128/87 B; 128/75
[58] Field of Search ..................... 128/69, 78, 75, 134, 128/133, 781, 68, 82, 84 R, 84 C, 87 B

[56] References Cited

U.S. PATENT DOCUMENTS

| 2,735,424 | 2/1956 | Benjamin | 128/87 B |
| 2,736,314 | 2/1956 | Hale | 128/87 B |
| 3,724,452 | 4/1973 | Nitschke | 128/75 |
| 3,771,513 | 11/1973 | Valazquez | 128/78 |
| 3,871,367 | 3/1975 | Miller | 128/87 B |
| 4,285,336 | 8/1981 | Oebser et al. | 128/78 |
| 4,383,523 | 5/1983 | Schurman | 128/75 |

FOREIGN PATENT DOCUMENTS 1064 of 1852 United Kingdom .................. 128/78

OTHER PUBLICATIONS

Two-Page advertisement of Durr-Fillauer Medical, Inc. Entitled "Low Profile Neck Ring".
One-Page Durr-Fillauer Medical, Inc. advertisement Entitled "Low Profile Neck Ring C.T.L.S.O." Bearing a date of Dec. '82.
One Page of a brochure of Pope Brace, Orthopedic Division, Parke-Davis, with a copright date of 1980 to Warner Lambert Co.
Article entitled "A New Cervical Neck Ring for the Idiopathic Scoliosis C.T.L.S.O." Appearing on pp. 50-54 of a Booklet entitled Orthotics and Prosthetics, Spring, 1984, vol. 38, No. 1, of the American Orthotic and Prosthetic Association.

Primary Examiner—Edgar S. Burr
Assistant Examiner—Tonya Eckstine
Attorney, Agent, or Firm—Luke J. Wilburn, Jr.

[57] ABSTRACT

A low profile neck ring for attachment to supporting structure of an orthopedic body brace employed to treat curvature of the spine comprising a resiliently deformable unitary collar plate for closely surrounding the lower neck portion of a wearer, the plate having an anterior yoke portion for overlying the sternum of the wearer and unitarily interconnecting a pair of elongate web portions having a lateral width substantially greater than the thickness of the plate, the web portions initially extending upwardly and rearwardly of the yoke portion to overlie the clavicle areas on either side of the neck of the wearer and having further posterior web portions extending downwardly and terminating in abutting relation to overlie the area of the spine adjacent the scapula of the wearer. Releasable fastening means rigidly interconnect the abutting end portions of the web portions of the collar plate to prevent their relative movement, and means on the yoke portion of the plate and on each posterior end portion of the web portion of the collar plate rigidly interconnect the neck ring to the upstanding support bars of a body brace. The unitary collar plate is preferably formed of rigid plastic material and is of sufficient lateral width in its web portions to resist displacement in use on the body brace.

9 Claims, 4 Drawing Figures

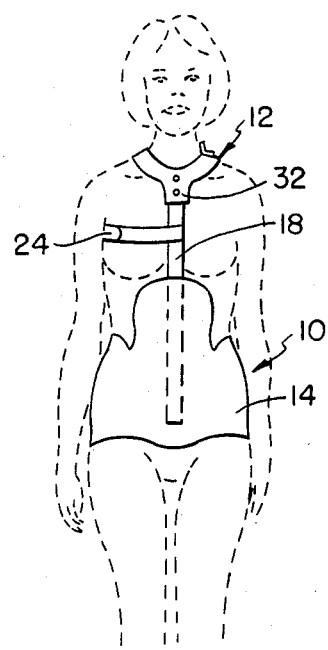
FIG - 1 -
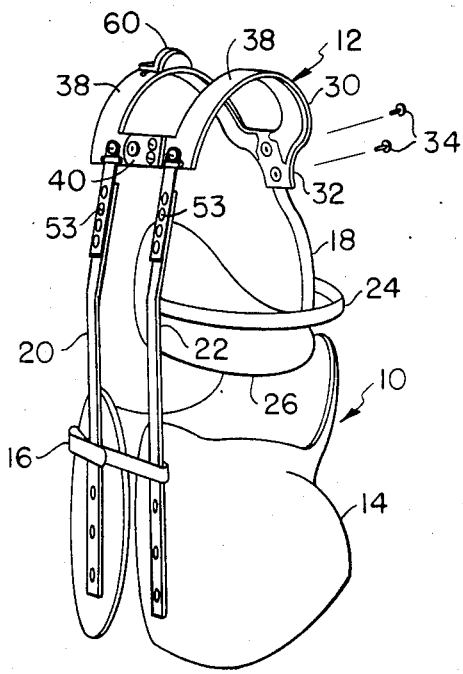
FIG. - 2 -

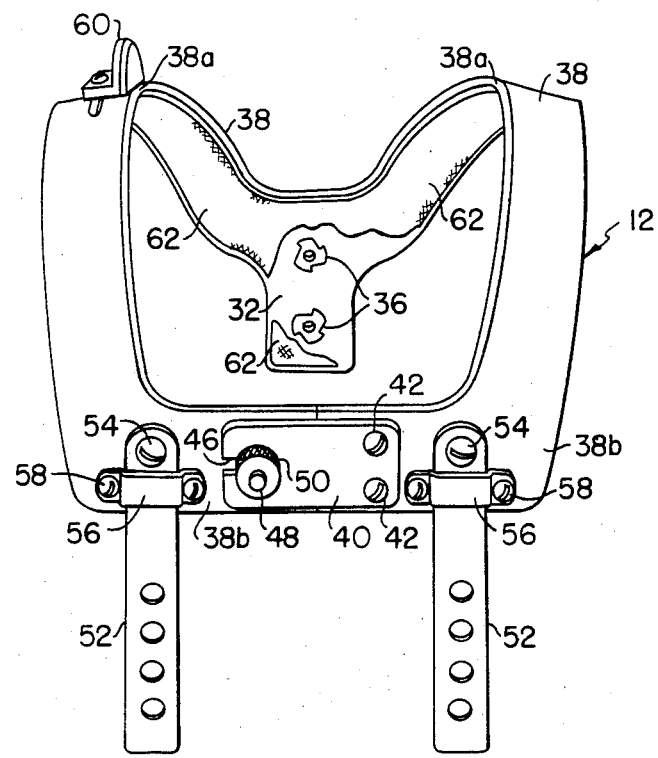
FIG. -3-
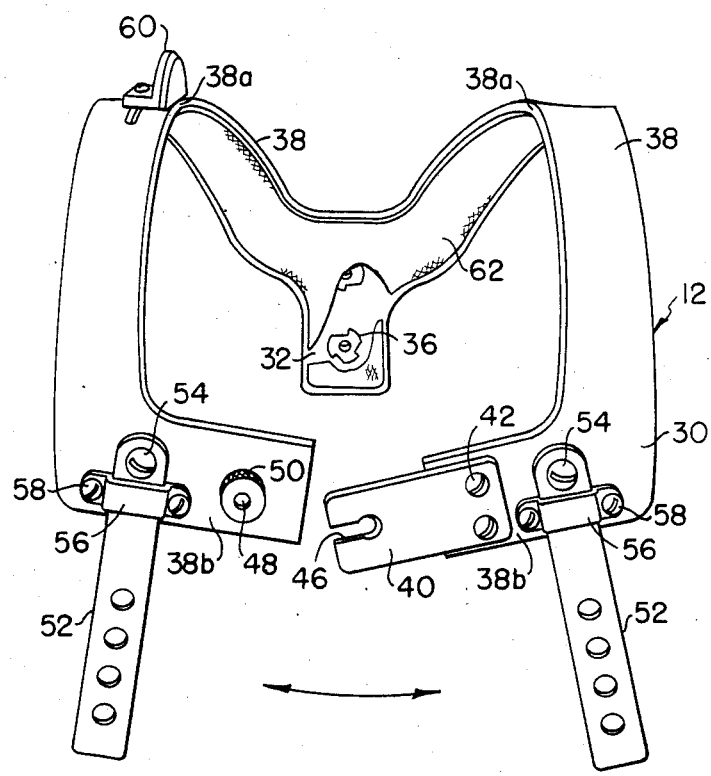
FIG. -4-

LOW PROFILE NECK RING ORTHOSIS

The present invention is directed to an improved low profile neck ring for use in orthopedic braces and, more particularly, braces of the Milwaukee brace type which are employed to treat scoliosis and kyphosis of the spine.

BACKGROUND OF THE INVENTION

Orthopedic braces have long been employed to treat and correct curvature of the spine (scoliosis and/or kyphosis). Typical of such braces is the so-named Milwaukee brace which consists of a lower torso-encircling girdle composed of molded plastic, leather, or relatively rigid light-weight material which fastens about the body to anchor and support a plurality of rigid metal bars which extend upwardly to the neck and head area of the wearer. The metal bars in turn support one or more pads which engage and apply pressure to the wearer's body at desired locations to counter a particular curvature of the spine. The metal bars of the Milwaukee brace also support a metal ring which surrounds the neck or head of a patient. On this neck ring, mandible and occipital supports are mounted.

Early metal neck rings of the prior art have been located adjacent the jaw of the patient to suppor pads which lift and align the head and neck. More recently, a low profile metal neck ring has been designed to surround the lower portion of the neck of the wearer adjacent the clavicle, sternum, and spine of the scapular. Body-engaging pads attached to the low profile neck ring apply pressure in desired directions against the neck adjacent the spine of the patient. As an example, a corrective body brace having a low profile neck ring attachment may employ pads which apply pressure against the left hip, right rear rib cage, and left side of the neck to create a three-point corrective force to counter a left curvature of the spine of the wearer.

Low profile neck rings are desirable in reducing the emotional trauma a patient may face in use of an orthosis of the type described. Low profile neck rings minimize the stress on the patients in terms of brace. Low profile neck ring constructions of the prior art comprise an anteriorly located metal mounting plate for attachment to an anterior upright support bar of a rear-opening girdle. Attached to the mounting plate in journals for rotational adjustment about their respective longitudinal axes are a pair of rigid metal rods of circular cross-section which are curved to extend rearwardly on opposite sides of the neck of the wearer. The ends of the two metal rods are interconnected at a posterior body position by a releasable metal fastening bracket. The fastening bracket is in turn rotatably attached by fastening pins to two anteriorly positioned, spaced upright bars of the girdle. Suitable body-engaging pads are adjustably attached to the neck ring rods at desired locations to engage the body of the wearer. The body brace is removed from the patient's body by opening the rear of the girdle and the anteriorly located fastening bracket of the neck ring, with rotation of the two neck ring rods about their journalled connections to the anterior mounting plate to open the neck ring for passage of the head of the patient therethrough.

Although the described low profile metal neck ring construction of the body brace provides a close-fitting, more attractive cosmetic appearance than the earlier, higher positioned metal neck rings, the low profile ring lacks desired stability of support in use. Because of the necessary rotational attachment of the neck ring rods on the anterior mounting plate to permit opening and removal of the ring from the neck, the ring tends to become laterally displaced relative to a vertical mid-line of the body when wearer body movement produces torque forces about the rod journals. Such displacement results in improper positioning of the neck ring on the body and improper application of corrective forces to the patient. Such low profile neck rings of the prior art, as described, are manufactured by Durr-Fillauer Company and are described on pages 50–54 of *Orthotics and Prosthetics,* Spring 1984, Volume 38, No. 1, published by The American Orthotic and Prosthetic Association.

BRIEF OBJECTS OF THE INVENTION

It is an object of the present invention to provide an improved low profile neck ring for use as an attachment to a supporting orthopedic body brace of the Milwaukee brace type to treat and correct scoliosis and/or kyphosis of the spine.

It is another object to provide an improved low profile neck ring attachment which is constructed and designed to resist relative displacement on a body brace during use by a wearer, and to maintain proper application of corrective forces and pressure against selected points on the wearer's body to adjust the spine.

It is another object to provide an improved low profile neck ring attachment which may be conformed closely to the upper body and neck area of a wearer to provide improved cosmetic appearance and comfort in wear.

It is a further object of the invention to provide an improved body brace having a low profile neck ring which has improved resiliency, strength, and resistence to lateral displacement by forces applied to the neck ring and brace during normal wear by a patient.

BRIEF SUMMARY OF THE INVENTION

The present invention comprises an improved low profile neck ring for attachment to the supporting structure of an orthopedic body brace employed to correct curvature of the spine. The neck ring comprises a resiliently deformable unitary collar plate for closely surrounding the lower portion of the neck of a wearer to support body-engaging pads thereon. The plate includes an anterior yoke portion which overlies the sternum of the wearer and unitarily interconnects a pair of elongate web portions having a width substantially greater than their thickness. The web portions extend rearwardly of the yoke portion to overlie the clavicle, or collar bone, areas on either side of the neck of the wearer. Posterior ends of the web portions terminate in abutting relation and overlie the spine adjacent the scapula of the wearer. The ends of the web portions are rigidly interconnected by fastening means which prevent their relative movement. Means are provided to rigidly fasten the yoke portion and the end portions of each web portion of the collar plate to upstanding rigid support bars of the body brace to prevent relative movement therebetween. The neck ring is thus structured and anchored to resist lateral displacement during its use about a vertical centerline of the body of the wearer. The collar plate is preferably formed of a light-weight, high-strength, resiliently deformable plastic material, such as high-density polyethylene.

The low profile collar is lined with a foam pad and constructed in such a manner as to be sufficiently rigid to resist lateral displacement when forces are exerted thereon during use and wear by the patient, but is sufficiently deformable to permit release of the posterior ends of the web portions of the collar and their displacement to remove the neck ring from the neck of the wearer.

BRIEF DESCRIPTION OF THE DRAWINGS

The above, as well as other objects of the invention, will become more apparent, and the invention will be better understood from the following detailed description of preferred embodiments thereof when taken together with the accompanying drawings, in which:

FIG. 1 is a front elevation view of an orthopedic body brace incorporating the improved low profile neck ring of the present invention, and showing the brace in typical position on the body of a wearer;

FIG. 2 is an enlarged rear perspective view of the low profile neck ring of the present invention, and showing its attachment to upright supporting bars of the body brace of FIG. 1;

FIG. 3 is a further enlarged rear perspective view of the low profile neck ring of the present invention; and FIG. 4 is a similar view to that of FIG. 3, but showing the neck ring in opened position to permit its removal from the neck and head of a wearer.

DETAILED DESCRIPTION OF PREFERRED EMBODIMENTS

Referring more specifically to the drawings, FIG. 1 shows, in front elevation, an orthopedic body brace 10 of the Milwaukee type incorporating the low profile neck ring 12 of the present invention. Such a brace is typically employed to treat and correct scoliosis and/or kyphosis of the spine in children and adults. As seen in FIGS. 1 and 2, the orthopedic body brace 10 comprises a posterior-opening girdle 14 formed of high-strength, resiliently deformable material, such as molded plastic, which has a suitably padded interior and is secured about the lower torso of the body of a wearer by a posteriorly located fastening means, such as a flexible strap 16. Rigidly attached to the front and rear of the girdle are upstanding metal bars, one of which 18 extends centrally upwardly adjacent the anterior or chest portion of the wearer's body and two of which 20, 22 (FIG. 2) are positioned posteriorly to extend upwardly adjacent the posterior or back of the wearer. Supportably attached to the bars 18, 20 and a flexible strap 24 connecting front and rear bars 18, 20 is a cushioned pressure pad 26 which is located to engage a desired portion of the wearer's body, such as the right rear back portion of the body.

As best seen in FIG. 2, the low profile neck ring 12 of the present invention is rigidly attached to the upper ends of the bars of the body brace to surround the lower neck portion of the wearer. Referring to FIGS. 1–4, the neck ring comprises a resiliently deformable, unitary collar plate 30 closely surrounding the neck portion of the body of the wearer. The plate is formed of lightweight, resiliently deformable high-strength material, such as a high-density polyethylene. Unitary collar plate 30 includes a flat anterior yoke portion 32 for overlying the sternum of the wearer. The yoke portion 32 is rigidly fixed to the anterior upright metal bar 18 of the body brace by a pair of threaded screws 34 which are received in T-nuts 36 which have been press-fitted into the plastic yoke portion of the colla plate. The anterior yoke portion 32 of the collar plate is thus anchored securely against relative movement on the supporting upright bar 18 of the body brace. Yoke portion 32 is unitarily formed with and interconnects a pair of elongate web portions 38 of the plate which extend outwardly, upwardly, and rearwardly of the yoke portion to closely overlie the collar bones on either side of the neck of the wearer. Inner edges 38a (FIGS. 3 & 4) of the web portions may flare slightly upwardly to conform closely to the contour of the trapezoid muscles of the neck. Elongate web portions 38 have posteriorly positioned end portions 38b which form right angles with the main length of the web portions and terminate in abutting relationship to overlie the spine adjacent the scapula of the body of the wearer. The end portion 38b of the web portions are firmly secured in abutting relation against relative movement with respect to each other by a metal fastening plate 40 secured by threaded screws 42 and T-nuts (not seen) to the end of one of the web portions. The other end of fastening plate 40 is slotted at 46 (FIG. 4) to be grippingly engaged by a threaded bolt 48 and knurled locking knob 50 secured to the end of the other web portion.

Rigidly attached to the posterior portion of each web portion on either side of fastening plate 40 are downwardly extending metal bars 52 which are adjustably interconnected by locking bolts 53 at their lower end portions to the upstanding support bars 20, 22 of the body brace 10. To prevent relative lateral movement of the posterior portion of the low profile neck ring, the metal bars 52 are attached to posterior portions of the web portions by threaded bolts 54 and T-nuts, and by a spaced, channel-shaped clamp 56 which overlies each bar 52 and is secured by threaded bolts 58 to the web portions of the collar plate.

Adjustably attached to the surface of the left web portion of the collar plate is a body-engaging pressure pad 60. As shown, with portions broken away, the undersurface of the collar plate is covered with a resilient foam layer 62 to cushion the ring in contact with the wearer's body.

As can be seen from the drawings, the elongate web portions 38 of the unitary collar plate which extend rearwardly on either side of the neck of the wearer to overlie the collar bone areas have a width, or lateral dimension, which is substantially greater than the thickness of the plate. Typically, the plate 30 may have a thickness of about 0.20 inch, and the lateral width of each web portion is about 1⅛ inches, or greater.

By firmly anchoring the anterior yoke portion 32 and the posterior end portions 38b of the neck ring to the upstanding support bars 18, 20, 22 of the body brace, and by forming the collar plate 30 of a unitary resiliently deformable plastic of substantial widthwise, or lateral dimension, relative to the vertical centerline of the body, the neck ring thus provides a fixed positional support for the neck pressure pad 60 to resist its displacement by forces applied thereto during normal use. The rigidly mounted neck ring is, however, sufficiently deformable that the web portions 38 of the collar plate can be separated upon release of the fastening plate 40 and girdle strap 16 to permit passage of the head of the wearer therethrough when donning and removing the body brace from the body of the wearer. The collar plate is also resiliently deformable in a posterior-anterior direction to permit it to be closely positioned adjacent the sternum and spine adjacent the scapula of the wearer.

The low profile neck ring of the present invention may be made in plural sizes, e.g., small, medium, large, and extra-large, to accommodate various sizes of infants, children, and adult wearers. Typically, the polyethylene unitary collar plate may be die cut from heat-formable, high-density polyethylene sheet material and shaped on a suitable shaping surface in a vacuum-forming operation. High-density plastic resin material suitable for formation of the collar plate may be Chemplex ® polyetnylene 5602 manufactured by Chemplex Company of Rolling Meadows, Ill.

In a body brace with the improved low profile neck ring, as illustrated in the drawings, padding is located adjacent the lower left hip of the wearer, the right rear back portion of the wearer, and the lower left neck portion of the wearer to provide a three-point application of pressure for corrective adjustment or treatment of a left curvature of the spinal column. For correction of a right curvature of the spinal column, the padding and pressure application would be reversed to lower right hip, left back, and lower right neck portion of the wearer. The exact placement of pressure-applying pads would be determined during fitting of the body brace on the particular patient by the orthodist or orthopedic technician, depending upon the particular condition of the patient to be treated. Similarly, the angular position of the short depending metal bars 52 on the posterior of the collar plate would be determined and fixed on the collar plate by clamps 56 during final adjustment and fitting of the brace on a patient.

That which is claimed is:

1. An improved low profile neck ring for attachment to supporting structure of an orthopedic body brace employed to treat curvature of the spine comprising a resiliently deformable unitary collar plate for closely surrounding the lower neck portion of a wearer, said plate being a single unit having a anterior yoke portion for overlying the sternum of the wearer and having a pair of elongated web portions having a lateral width substantially greater than the thickness of the plate, said web portions initially extending upwardly and rearwardly from the yoke portion to overlie the clavicle areas on either side of the neck of the wearer, then extending over the shoulders and terminating in posteriorly located end portions, said end portions in abutting relation to overlie the area of the spine adjacent the scapula of the wearer, releasable fastening means rigidly interconnecting the abutting end portions of the web portions of the collar plate to prevent their relative movement, means on said yoke portion of the plate for rigidly attaching the collar plate to an upstanding support bar of a body brace, and means for attaching each posterior end portion of each web portion of the collar plate rigidly to an upstanding support bar of a body brace.

2. A low profile neck ring as defined in claim 1 wherein said collar plate is formed of plastic material.

3. A low profile neck ring as defined in claim 2 wherein said plastic material is polyethylene.

4. A low profile neck ring as defined in claim 2 wherein said means on said yoke portion for attaching the yoke portion of the collar plate to an upstanding support bar of a body brace comprises a pair of spaced fastening means located on said yoke portion to engage and attach the yoke portion of the collar plate to the support bar to prevent relative movement between the yoke portion and support bar.

5. A low profile neck ring as defined in claim 2 wherein said means for rigidly interconnecting the posterior end portion of each web portion of the collar plate to an upright support bar of a body brace includes a rigid metal bar attached to each posterior end portion and means fixing the position of each metal bar on each posterior end portion.

6. A low profile neck ring as defined in claim 2 including cushioning mean on the undersurface of the collar plate for engaging the body of a wearer.

7. A low profile neck ring as defined in claim 2 wherein said collar plate is about 0.2 inches thick and the lateral width of each of said web portions is at least about $1\frac{1}{8}$ inches to resist lateral displacement.

8. A body brace for treating curvature of the spine, comprising a rear-opening, support girdle for surrounding attachment to the lower torso of the body of a wearer, an anterior, upstanding rigid support bar attached to the girdle, a pair of spaced posterior upstanding support bars attached to the girdle, and a low profile neck ring rigidly attached to respective upper end portions of the anterior and posterior support bars of the brace to surround the lower portion of the neck of a wearer in close proximity thereto, said neck ring including a resiliently deformable, unitary collar plate for surrounding the lower neck portion, said plate having a yoke portion for overlying the sternum of a wearer, means interconnecting the yoke portion rigidly to the anterior support bar of the body brace, and a pair of web portions extending upwardly and rearwardly from the yoke portion to overlie the clavicle areas on either side of the neck of the wearer, said web portions further extending downwardly and terminating in posterior end portions, said end portions being in abutting relation to overlie the area of the spine adjacent the scapula of the wearer, releasable fastening means for rigidly interconnecting the end portions of the web portions of the collar plate to prevent their relative movement, means attached to the posterior end portion of each web portion of the collar plate for rigidly interconnecting the posterior web end portion to a respective spaced posterior upstanding support bar of the body brace to prevent relative movement of the posterior end portions relative to the posterior upright support bars, a neck engaging pad attached to the collar, and said web portions of the collar plate having sufficient lateral width substantially greater than the plate thickness to resist lateral displacement by forces exerted thereon during use of the body brace.

9. A body brace as defined in claim 8 wherein said collar plate is formed of plastic material, and each of said web portions has a lateral width of at least about $1=$ inches.

* * * * *